United States Patent
Yazdanpanah et al.

(10) Patent No.: US 10,737,066 B2
(45) Date of Patent: Aug. 11, 2020

(54) LOOP CATHETER WITH ACTIVATION TETHER COUPLED TO PRE-FORMED LOOP STRUCTURE

(71) Applicant: St. Jude Medical, Cardiology Division, Inc., St. Paul, MN (US)

(72) Inventors: Mort Yazdanpanah, Minnetonka, MN (US); Zachary L. Helgeson, Richfield, MN (US); Warren Solom, Plymouth, MN (US); Renato Conedera, St. Louis Park, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 64 days.

(21) Appl. No.: 15/702,173

(22) Filed: Sep. 12, 2017

(65) Prior Publication Data

US 2018/0078738 A1    Mar. 22, 2018

Related U.S. Application Data

(60) Provisional application No. 62/413,074, filed on Oct. 26, 2016, provisional application No. 62/396,169, filed on Sep. 18, 2016.

(51) Int. Cl.
*A61B 5/0402* (2006.01)
*A61B 18/14* (2006.01)
(Continued)

(52) U.S. Cl.
CPC ........ *A61M 25/0147* (2013.01); *A61B 5/0422* (2013.01); *A61B 5/6856* (2013.01);
(Continued)

(58) Field of Classification Search
CPC ........ A61B 18/1492; A61B 2018/1435; A61B 2018/1467; A61B 5/0422; A61B 5/042;
(Continued)

(56) References Cited

U.S. PATENT DOCUMENTS 5,111,829 A    5/1992   De Toledo
5,827,278 A *  10/1998  Webster, Jr. ........ A61B 18/1492
                                                       606/41
(Continued)

FOREIGN PATENT DOCUMENTS

EP    2260772 A1    12/2010
JP    S61153605 A    7/1986
(Continued)

OTHER PUBLICATIONS

ED Special Welding Materials (website) Dec. 5, 2011 https://www.bakersgas.com/weldmyworld/2011/12/05/tips-welding-inconel/ (Year: 2011).*

(Continued)

*Primary Examiner* — Eun Hwa Kim
*Assistant Examiner* — Brian M Antiskay
(74) *Attorney, Agent, or Firm* — Armstrong Teasdale LLP

(57) ABSTRACT

Disclosed is a coupling for use in a looped medical device, such as a loop catheter. A sleeve is fitted onto a distal portion of an activation wire and a shape-memory wire is positioned alongside the sleeved activation wire. The sleeve is welded onto the activation wire to hold the sleeve onto the activation wire and is also welded onto the shape-memory wire that is positioned alongside the activation wire, thereby affixing the activation wire to the shape-memory wire. Also disclosed is an activation wire for use in a catheter. The activation wire includes a proximal section, and a distal section having at least a partial loop. The activation wire includes a connection section on the distal section, where the connection (Continued)

section is linear, and where the external surface of the connection section has a higher coefficient of friction than at least some of the remaining portion of the actuation wire that is housed within the catheter shaft.

6 Claims, 12 Drawing Sheets

(51) Int. Cl.

| | | |
|---|---|---|
| *A61M 25/01* | (2006.01) | |
| *B23K 26/211* | (2014.01) | |
| *A61B 5/042* | (2006.01) | |
| *A61B 5/00* | (2006.01) | |
| *A61M 25/00* | (2006.01) | |
| *B23K 26/323* | (2014.01) | |
| *A61B 17/00* | (2006.01) | |
| *A61B 18/00* | (2006.01) | |
| *A61N 1/05* | (2006.01) | |

(52) U.S. Cl.
CPC .... *A61M 25/0009* (2013.01); *A61M 25/0133* (2013.01); *B23K 26/211* (2015.10); *A61B 18/1492* (2013.01); *A61B 2017/00323* (2013.01); *A61B 2017/00477* (2013.01); *A61B 2017/00858* (2013.01); *A61B 2017/00867* (2013.01); *A61B 2018/00351* (2013.01); *A61B 2018/00577* (2013.01); *A61B 2018/1407* (2013.01); *A61M 2025/015* (2013.01); *A61M 2025/0163* (2013.01); *A61M 2205/0266* (2013.01); *A61N 1/0592* (2013.01); *B23K 26/323* (2015.10)

(58) Field of Classification Search
CPC ........... A61B 2017/00867; A61B 2017/00053; A61B 2017/003; A61B 5/6851; A61B 5/6852; A61M 25/09
USPC ........ 600/372–374, 381, 433–435, 466, 481, 600/508–509; 604/95.04, 523, 528, 530; 606/32, 41; 607/115–116, 122–131
See application file for complete search history.

(56) References Cited

U.S. PATENT DOCUMENTS

| | | | |
|---|---|---|---|
| 6,066,125 A * | 5/2000 | Webster, Jr. ........... | A61B 5/015 604/528 |
| 6,542,781 B1 * | 4/2003 | Koblish .............. | A61B 18/1492 607/122 |
| 6,875,949 B2 | 4/2005 | Hall | |
| 7,606,609 B2 | 10/2009 | Muranushi et al. | |
| 8,369,923 B2 | 2/2013 | De La Rama et al. | |
| 8,600,472 B2 * | 12/2013 | Govari ................ | A61B 5/0422 600/374 |
| 8,795,241 B2 * | 8/2014 | O'Connell ......... | A61B 1/00087 604/264 |
| 8,798,706 B2 * | 8/2014 | Kim .................. | A61B 18/1492 600/374 |
| 9,387,034 B2 * | 7/2016 | Okada .................... | A61B 18/14 |
| 2002/0004631 A1 * | 1/2002 | Jenkins .............. | A61B 18/1492 600/374 |
| 2005/0010095 A1 * | 1/2005 | Stewart .............. | A61B 18/1492 600/374 |
| 2007/0244413 A1 | 10/2007 | Biggins | |
| 2007/0270679 A1 * | 11/2007 | Nguyen ............ | A61M 25/0043 600/373 |
| 2008/0290076 A1 | 11/2008 | Sheldon et al. | |
| 2010/0286684 A1 * | 11/2010 | Hata .................. | A61B 18/1492 606/33 |
| 2011/0004087 A1 | 1/2011 | Fish et al. | |
| 2016/0114132 A1 * | 4/2016 | Chmielewski ........ | A61M 39/14 604/95.04 |
| 2017/0202468 A1 | 7/2017 | Nemec et al. | |

FOREIGN PATENT DOCUMENTS

| | | |
|---|---|---|
| JP | H09201367 A | 8/1997 |
| JP | 2005124697 A | 5/2005 |
| JP | 2005130965 A | 5/2005 |
| JP | 2010075530 a | 4/2010 |
| JP | 2015023925 A | 2/2015 |
| JP | 2015083224 A1 | 4/2015 |
| WO | 03063940 A2 | 8/2003 |
| WO | 2010068804 A1 | 6/2010 |
| WO | 2010107798 A1 | 9/2010 |
| WO | 2012061935 A1 | 5/2012 |

OTHER PUBLICATIONS

Invitation to Pay Additional Fees, Partial Search Result, and Provisional Opinion Accompanying the Partial Search Result, for International Patent Application No. PCT/US2017/051151, dated Dec. 20, 2017, 13 pages.

* cited by examiner

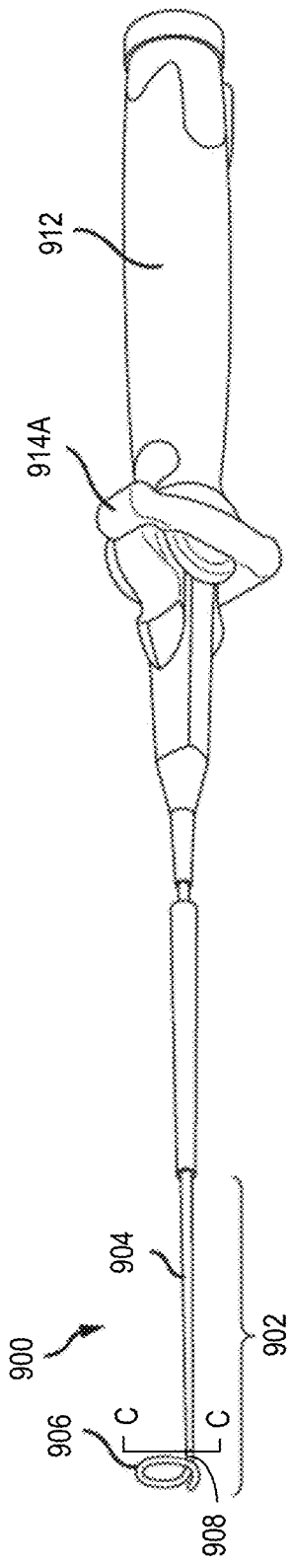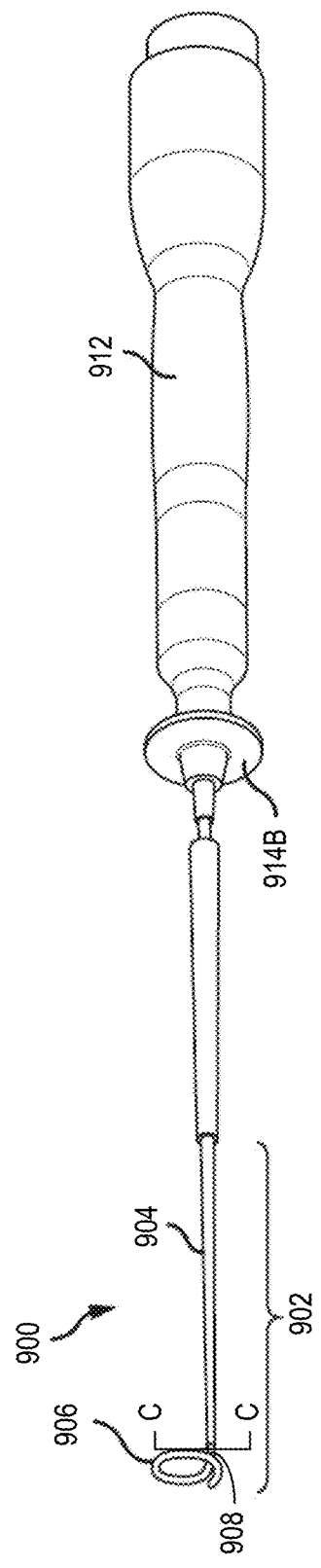
FIG. 9A
FIG. 9B

LOOP CATHETER WITH ACTIVATION TETHER COUPLED TO PRE-FORMED LOOP STRUCTURE

CROSS-REFERENCE TO RELATED APPLICATIONS

This application claims the benefit of U.S. Provisional Patent Application No. 62/396,169, filed Sep. 18, 2016, and U.S. Provisional Patent Application No. 62/413,074, filed Oct. 26, 2016, the contents of which are hereby incorporated by reference herein in their entirety.

BACKGROUND

The disclosure relates to catheters for use in medical procedures, such as electrophysiology diagnostic or therapy procedures, and manners for attaching dissimilar structures for catheter features.

Catheters are used for an ever-growing number of medical procedures, such as diagnostic, therapeutic, and ablative procedures, to name just a few examples. Typically, the catheter is manipulated through the patient's vasculature to the intended site, for example, a site within the patient's heart.

A typical electrophysiology catheter includes an elongate shaft and one or more electrodes on the distal end of the shaft. The electrodes may be used for ablation, diagnosis, or the like. One representative use of an electrophysiology catheter is for mapping the atrial regions of the heart, such as the pulmonary veins, which are often origination points or foci of atrial fibrillation. An electrophysiology mapping catheter may have a loop shape at its distal end, oriented in a plane generally orthogonal to the longitudinal axis of the catheter shaft, which allows the loop to surround ostia such as the pulmonary vein ostia, or to otherwise cover a greater surface area than other catheters such as linear catheters.

BRIEF SUMMARY

The disclosure is directed to facilitating the activation of a distal catheter feature, such as adjusting a radius of a loop portion of catheter, adjusting a relative angle between a loop portion of a catheter and the catheter shaft, or other distal catheter manipulations. In one representative embodiment, an improved mating between an activation tether (e.g., activation wire) and a distal loop portion of a catheter is provided. In another representative embodiment, a manner of connecting a distal portion of an activation tether and a distal portion of the loop structure is provided, where activation of the activation tether enables modification of the radius of the distal loop portion in response to manipulation of the activation tether.

In one embodiment of the present disclosure, a wire coupling is provided that includes a first wire composed of a first material, a second wire composed of a second material, a sleeve configured to surround a portion of the first wire, and a laser weld affixing the sleeve to both the first wire and alongside the second wire.

In another embodiment of the present disclosure, a catheter is provided that comprises: (i) a shaft having a proximal portion and a distal portion; (ii) a pre-formed loop wire having a variable radius and positioned within the distal portion of the shaft to form a loop structure on the distal portion of the shaft; (iii) a stainless steel pull wire comprising a proximal section and a distal section; and (iv) a nickel superalloy sleeve dimensioned to fit over the distal section of the stainless steel pull wire, to connect to both the stainless steel pull wire and to the pre-formed loop wire with a laser weld.

In another embodiment of the present disclosure, there is provided a method of connecting a first wire and a second wire. The method comprises: (i) affixing a sleeve to the first wire having a first composition; (ii) positioning the second wire having a second composition alongside the first wire; and (iii) affixing the sleeve to the second wire, wherein the sleeve is configured to facilitate connection of the first wire to the second wire.

In another embodiment of the present disclosure, there is provided a method of connecting a stainless steel activation wire and a nickel titanium wire. The method comprises: (i) inserting a nickel superalloy hypo tube onto a distal portion of the stainless steel activation wire; (ii) laser welding the nickel superalloy hypo tube to a distal portion of the nickel titanium wire formed into at least a partial loop; and (iii) laser welding the nickel superalloy hypo tube onto the distal portion of the stainless steel activation wire.

In another embodiment of the present disclosure, an activation tether/wire for use with a catheter is provided. The activation wire includes a proximal section and a distal section having at least a partial loop (which may include a full loop). The activation wire is equipped with a sleeve having a composition capable of being affixed to the activation wire and also to a shape-memory wire to enable the activation wire to control a position of the shape-memory wire.

In another embodiment of the present disclosure, a catheter is provided that includes a shaft having a proximal portion and a distal portion. The catheter includes a pre-formed loop wire having a variable radius and positioned within the distal portion to form a loop structure on the distal portion of the shaft. The catheter further includes an activation wire having a proximal section and a distal section. The activation wire is made of a first material composition. The catheter includes a shape-memory wire having a looped portion with a distal end. The shape-memory wire is composed of a second material composition different than the first material composition of the activation wire. A sleeve is fitted over the distal section of the activation wire, and laser welded to both the activation wire and the adjacently-positioned shape-memory wire.

In another embodiment of the present disclosure, an activation wire for use in a catheter is provided. The activation wire comprises: (i) a proximal section; (ii) a distal section having at least a partial loop; and (iii) a connection section on the distal section, wherein the connection section is linear, and wherein an external surface of the connection section has a higher coefficient of friction than at least one of the proximal section and a remaining portion of the distal section that does not include the connection section.

In another embodiment of the present disclosure, a catheter is provided. The catheter comprises: (i) a shaft having a proximal portion and a distal portion; (ii) a pre-formed loop wire having a variable radius and positioned within the distal portion to form a loop structure on the distal portion of the shaft; (iii) an activation wire comprising a proximal section and a distal section having a formed loop structure, wherein the formed loop structure substantially corresponds to a shape of the pre-formed loop wire within the distal portion of the catheter, wherein the activation wire further comprises a linear connection section on the distal section having an external surface with a higher coefficient of friction than at least one of the proximal section and a remaining portion of the distal section that does not include the connection section; and (iv) a connecting element coupling the linear connection section of the activation wire to an aligned portion of the pre-formed loop wire to enable adjustment of the variable radius in response to manipulation of the activation wire.

The foregoing and other aspects, features, details, utilities, and advantages of the present disclosure will be apparent from a reading of the following description, claims, and accompanying figures.

BRIEF DESCRIPTION OF THE DRAWINGS

FIGS. 9A and 9B depict two representative embodiments of electrophysiology catheters into which the tether coupling embodiments described herein may be implemented;

DETAILED DESCRIPTION

For the sake of illustration, certain embodiments of the disclosure will be explained herein with reference to an electrophysiology catheter utilized in cardiac electrophysiology studies. It should be understood, however, that the present teachings may be applied to other catheters and medical devices having a manipulatable distal feature, such as an ablation or diagnostics catheter having a distal loop portion, distal balloon portion, distal splines, etc., where manipulation of that distal feature is involved.

Figure 1:
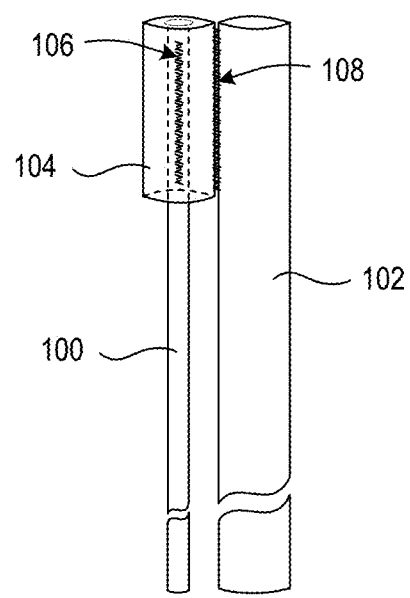
FIG. 1 illustrates an embodiment involving a first structure, such as a first tether or wire that is to be connected at some location to another tether or wire.

FIG. 1 illustrates an embodiment involving a first structure, such as a first tether or wire 100 that is to be connected at some location to another tether or wire 102. The wires 100, 102 may be connected at one or more points along their length. In one embodiment, the wires 100, 102 may be connected proximate an alignment of the ends of the wires 100, 102, such as at the free ends of the wires 100, 102.

In the illustrated embodiment, the wire 100 may have the same or a different diameter than the wire 102 at the area of connection. For example, in the illustrated embodiment, the wire 100 has a lesser diameter than the wire 102 to which it is to be connected.

When coupling wires together, such as coupling the free ends of wires 100, 102 together, it can be difficult to create sufficient bonds between the wires to keep them attached. For example, the wires can be crimped together, but depending on the material and characteristics of the wires being attached, such crimping can be ineffective when higher forces impact the crimped area.

One embodiment that addresses these and other issues is depicted in FIG. 1. In the illustrated example, the first and second wires 100, 102 are made of different materials that may not connect well by way of crimping, brazing, etc. Therefore, an appropriate sleeve 104 is positioned over the connectable region of at least one of the wires, such as wire 100. The sleeve 104 is made of a material that readily connects to both the wire 100 and to the wire 102 when welded or otherwise connected in an appropriate manner.

For example, in one embodiment the wire 100 represents an activation wire, such as a steering wire or other "pull wire" utilized in a catheter or other elongate medical device. In one embodiment, the activation or pull wire 100 is used to pull on another element in order to adjust the radius of a loop at the distal end of a loop catheter. For example, the pull wire 100 may be connected to the distal end of a shape-memory wire, such as wire 102, such that the distal end of the shape-memory wire 102 is pulled or curved in response to actuation (e.g., pulling) of the pull wire 100. In this manner, pulling the wire 100 will ultimately cause the shape-memory wire 102 to be pulled, thereby causing an associated catheter loop to decrease or otherwise adjust its radius and/or position.

In one particular example, the pull wire 100 of FIG. 1 may be made of a first material, such as stainless steel, and the shape-memory wire 102 may be made of a second material, such as nickel titanium (NiTi; also known as nitinol). Stainless steel does not effectively connect to nitinol. For example, joining stainless steel to nitinol is problematic because, among other things, the presence of iron promotes the formation of brittle Fe—Ti intermetallics. Embodiments described herein provide manners to facilitate a robust connection between such dissimilar components. In this example, the sleeve 104 is made from a material that is capable of connection to both dissimilar elements, i.e., stainless steel wire 100 and nitinol wire 102 in this example. Representative sleeve 104 compositions capable of facilitating attachment of the sleeve 104 to both the wires 100, 102 may include nickel superalloy hypo tubes, such as Nickel 600 or Inconel™ 600 (Huntington Alloys Corp.) or other nickel superalloy grades.

Keeping with the present example, in one embodiment the nickel hypo tube sleeve 104 is laser welded to stainless steel wire 100, as depicted by laser weld 106. For example, the attachment may be accomplished using fiber-delivered laser energy with an inert gas assist. In order to avoid the interference of intermetallics and ensure strong joints, the nickel superalloy hypo tube sleeve 104, such as an Inconel™ 600 hypo tube, can be utilized. While the size of the hypo tube or sleeve 104 varies depending on the application, in one embodiment where used in an electrophysiology catheter, the dimensions of the sleeve 104 are 0.016×0.10×100 inches (0.040×0.254×254 centimeters).

The sleeve 104 can be attached to the second wire 102, which in the present example includes nitinol. A sleeve 104, such as an Inconel™ 600 hypo tube, is capable of connecting to the nitinol wire 102 by way of welding, such as using fiber-delivered laser energy with an inert gas assist. FIG. 1 depicts the wire-to-wire laser weld 108 that holds the sleeved stainless steel wire 100 to the nitinol wire 102. In this manner, creating tension on the wire 100 will cause the properly connected nitinol wire 102 to also be pulled. As described below, when installed in a loop portion of a catheter, pulling the activation wire 100 pulls the properly connected wire 102 to enable the radius of the loop to be changed.

Further, in some embodiments, the wires 100, 102 may have different physical dimensions, such as the example of FIG. 1 where wire 100 has a smaller diameter than wire 102. In one embodiment, the sleeve 104 is sized to be approximately the same diameter as the wire 102 to which it will attach, which may facilitate the welding process.

Figure 2A:
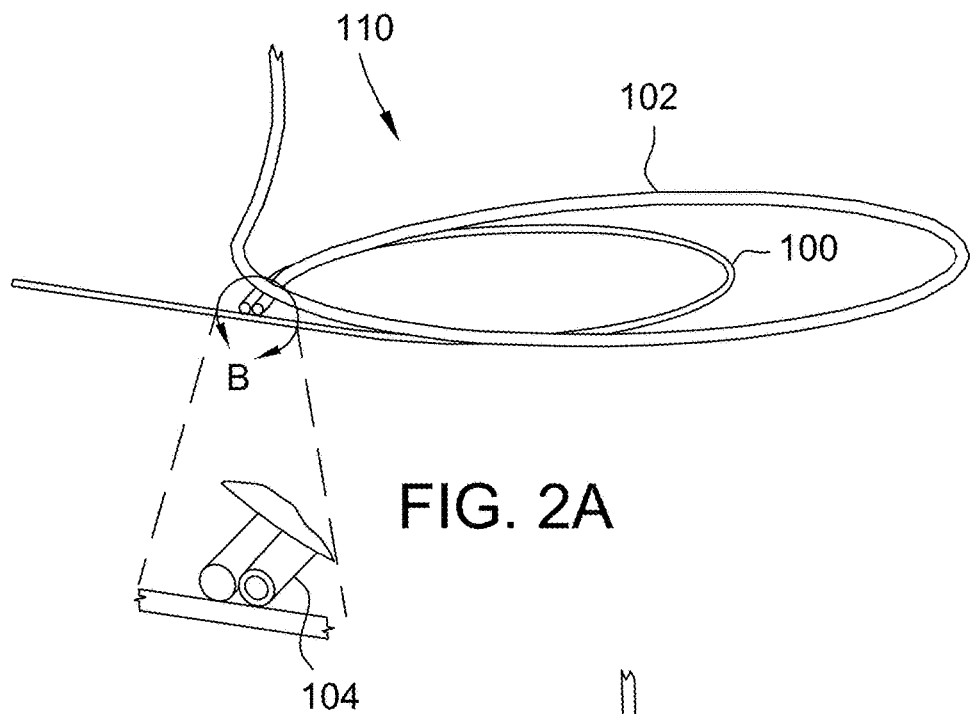
FIGS. 2A and 2B illustrate a loop feature that may be implemented at the distal portion of a catheter, such as an electrophysiology (EP) loop catheter.
Figure 2B:
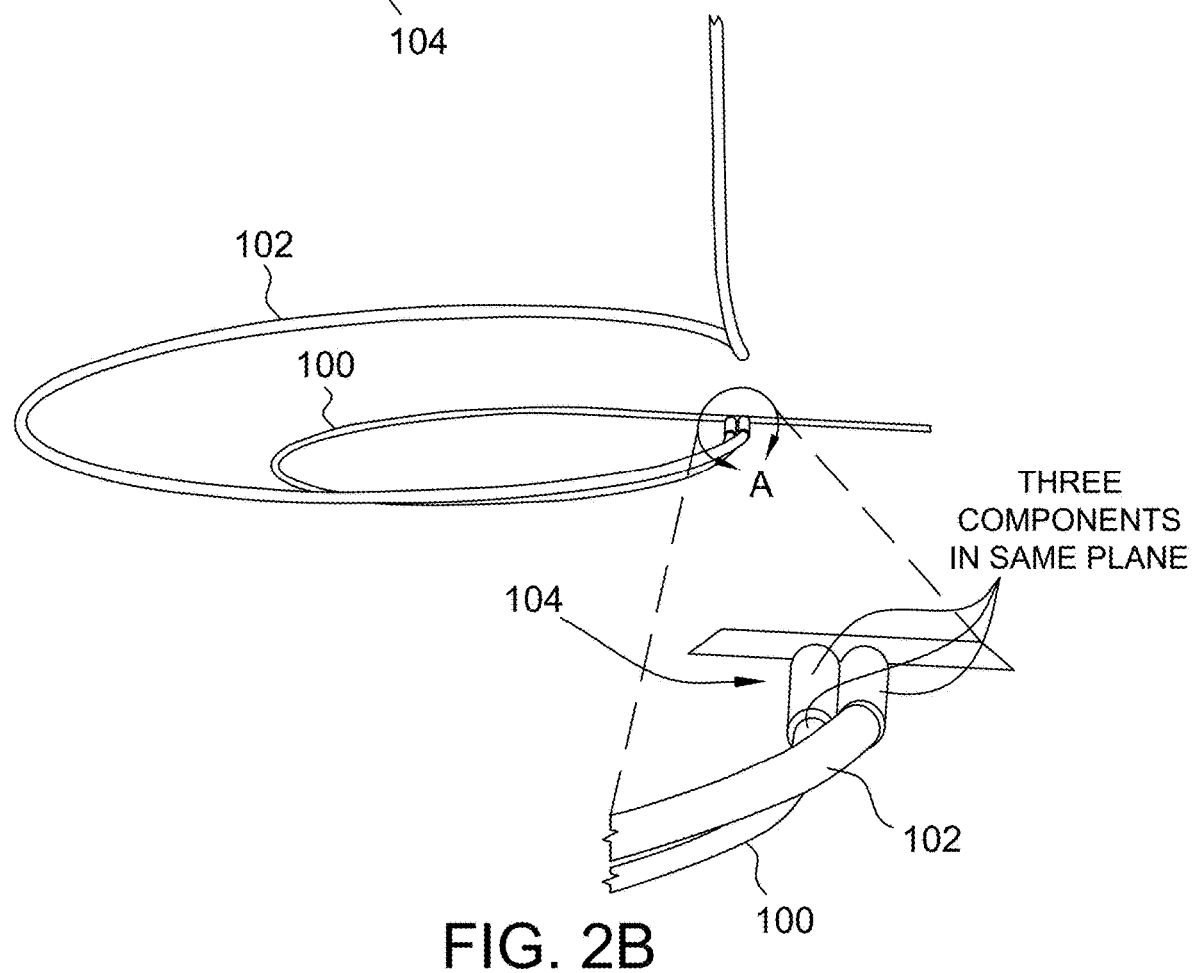

FIGS. 2A and 2B illustrate a loop feature 110 that may be implemented at the distal portion of a catheter, such as an electrophysiology (EP) loop catheter. In the illustrated embodiment, wire 102 represents the shape-memory wire described in connection with FIG. 1, such as a nitinol wire 102 that is pre-shaped into a loop corresponding to a natural state of the loop at the distal portion of the EP catheter. The wire 100 represents the activation wire or "pull wire" described in connection with FIG. 1. Thus, the distal portions of wires 100 and 102 are connected together as depicted in FIG. 2A. The expanded detail of area B is shown, where in one embodiment the wires 100, 102 and sleeve 104 are substantially flush at their ends, although they need not be flush with one another. Dimensions in FIG. 2A are merely an example of one particular size, while any size may be utilized.

FIG. 2B depicts the loop feature 110 of FIG. 2A from a different viewpoint. In this representative embodiment, and from this viewpoint, it can be seen that the two wires 100, 102 and the sleeve 104 are substantially in a common plane.

Figure 3A:
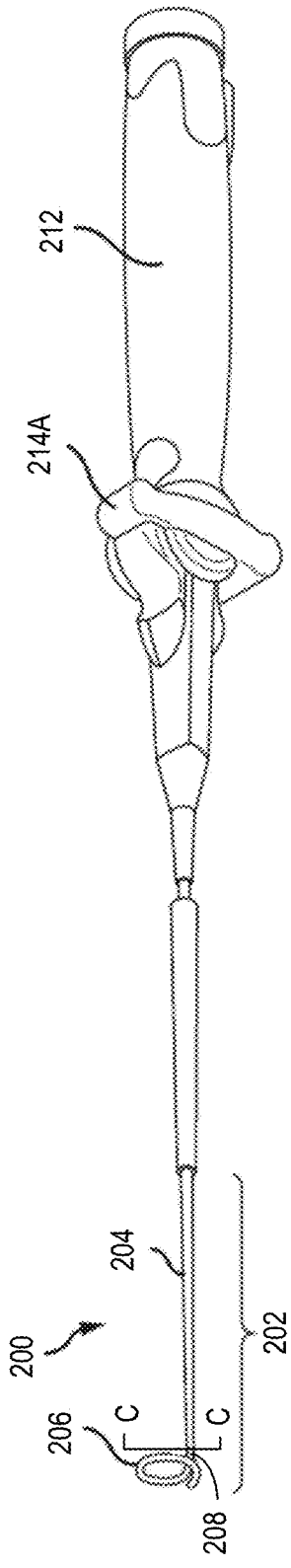
FIGS. 3A and 3B depict two representative embodiments of electrophysiology catheters into which the tether coupling embodiments described herein may be implemented.
Figure 3B:
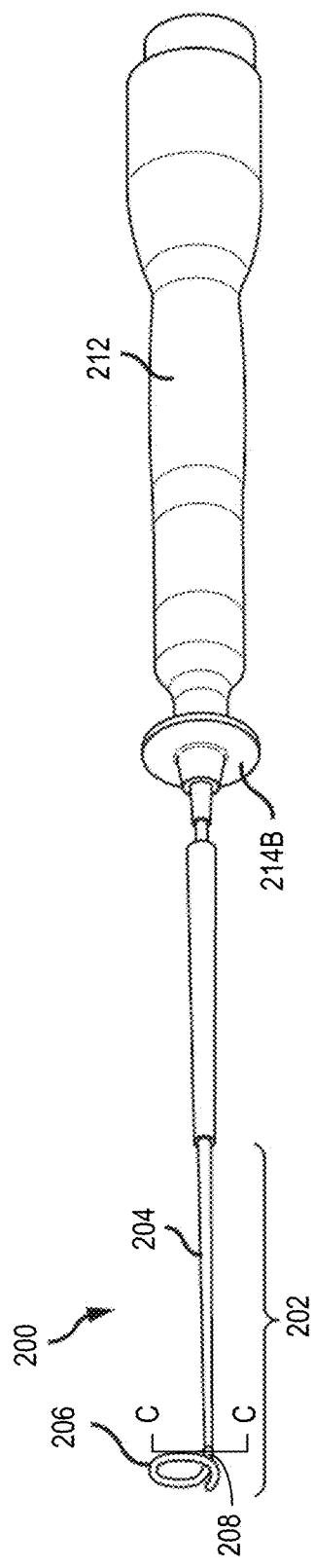

FIGS. 3A and 3B depict two representative embodiments of an electrophysiology (EP) catheter 200 into which the tether/wire coupling embodiments described herein and associated principles may be implemented. EP catheter 200 includes an elongate catheter body 202, which, in some embodiments, is tubular (e.g., it defines at least one lumen therethrough). Catheter body 202 includes a proximal region 204, a distal region 206, and a neck region 208 that offers a transition from proximal region 204 to distal region 206. In some embodiments, neck region 208 can include a coupling, such as described in U.S. provisional application No. 62/280,159, filed Jan. 19, 2016, which is hereby incorporated by reference as though fully set forth herein. The relative lengths of proximal region 204, distal region 206, and neck region 208 as depicted in FIGS. 3A and 3B are merely illustrative and may vary without departing from the spirit and scope of the instant disclosure. The overall length of catheter body 202 should be long enough to reach the intended destination within the patient's body.

Catheter body 202 may be made of a biocompatible polymeric material, such as PTFE tubing (e.g., TEFLON® brand tubing). Of course, other polymeric materials, such as fluorinated ethylene-propylene copolymer (FEP), perfluoroalkoxyethylene (PFA), poly(vinylidene fluoride), poly(ethylene-co-tetrafluoroethylene), and other fluoropolymers, may be utilized. Additional suitable materials for catheter body 202 include, without limitation, polyamide-based thermoplastic elastomers (namely poly(ether-block-amide), such as PEBAX™), polyester-based thermoplastic elastomers (e.g., HYTREL™), thermoplastic polyurethanes (e.g., PELLETHANE™, ESTANE™), ionic thermoplastic elastomers, functionalized thermoplastic olefins, and any combinations thereof. In general, suitable materials for catheter body 202 may also be selected from various thermoplastics, including, without limitation, polyamides, polyurethanes, polyesters, functionalized polyolefins, polycarbonate, polysulfones, polyimides, polyketones, liquid crystal polymers and any combination thereof. It is also contemplated that the durometer of catheter body 202 may vary along its length. The basic construction of catheter body 202 will be familiar to those of ordinary skill in the art, and thus will not be discussed in further detail herein except to the extent necessary to understand the instant disclosure.

Figure 3C:
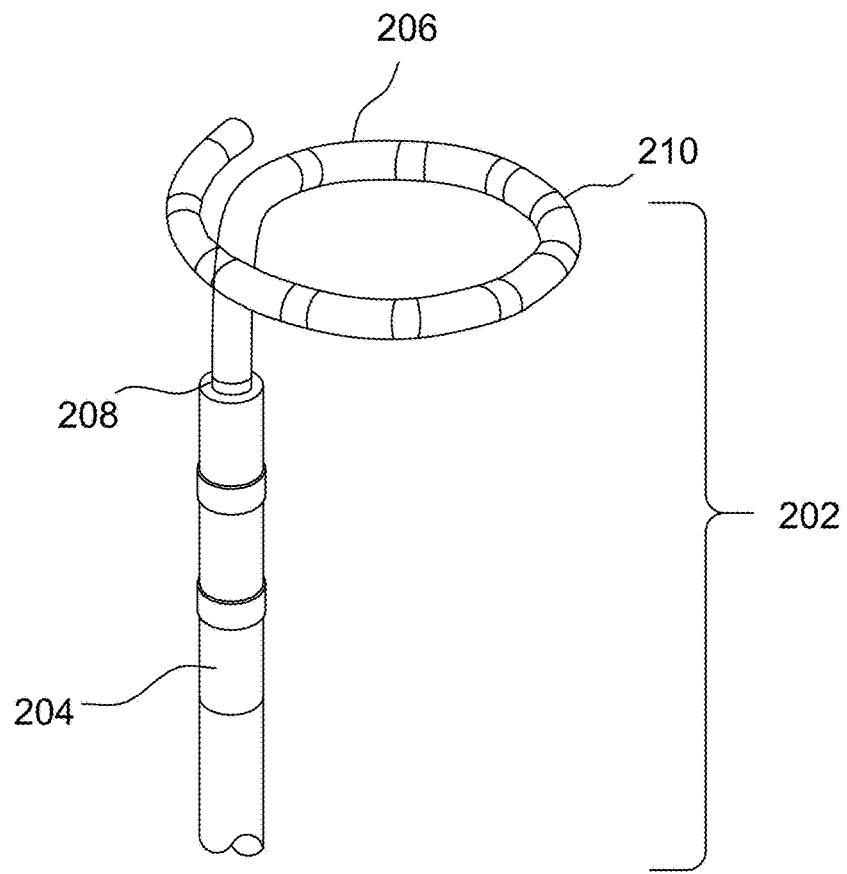
FIG. 3C illustrates a representative distal region of a catheter having multiple electrodes and being predisposed into at least a partial loop.

As seen in FIG. 3C, distal region 206 of catheter body 202 can be predisposed into at least a partial loop. This loop shape allows distal region 206 to conform to the shape, for example, of a pulmonary vein ostium. The partial loop may take a number of configurations, depending on the intended or desired use of EP catheter 200, consistent with the present teachings. Therefore, it should be understood that the loop configuration depicted in FIG. 3C is merely illustrative.

FIG. 3C also illustrates that distal region 206 can include a plurality of electrodes 210 disposed thereon. Electrodes 210 may be ring electrodes or any other electrodes suitable for a particular application of EP catheter 200. For example, where EP catheter 200 is intended for use in a contactless electrophysiology study, electrodes 200 may be configured as described in U.S. application Ser. No. 12/496,855, filed 2 Jul. 2009, which is hereby incorporated by reference as though fully set forth herein. Of course, in addition to serving sensing purposes (e.g., cardiac mapping and/or diagnosis), electrodes 200 may be employed for therapeutic purposes (e.g., cardiac ablation and/or pacing).

Referring again to FIGS. 3A and 3B, a handle 212 is coupled to catheter body 202, for example at the proximal end of proximal region 204. Handle 212 can include suitable actuators (e.g., actuator 214A in FIG. 3A; actuator 214B in FIG. 3B) to control the deflection of catheter body 202, for example as described in U.S. Pat. No. 8,369,923, which is hereby incorporated by reference as though fully set forth herein. Actuators 214A or 214B, or other actuators (not shown) may be utilized to alter the radius of the distal region 206. For example, an actuator different from actuators 214A, 214B may be included on the handle where manipulation of this actuator causes a loop in the distal region 206 of the catheter 200 to increase or decrease. Further, other mechanisms may be utilized to actuate the loop structure, such as robotic mechanisms.

In embodiments described herein, the radius of curvature of the loop of distal region 206 may be adjustable. For example, in one embodiment, the curvature is adjustable in order to conform to the varying sizes of pulmonary vein ostia. This additional control may be provided, for example, via the use of an activation wire, such as activation wire 100, shown in FIG. 3D, that is adapted to alter the radius of curvature of the loop of distal region 206. As previously noted, one suitable material for activation wire 100 is stainless steel or primarily stainless steel, though other materials can be employed without departing from the spirit and scope of the instant disclosure.

In some embodiments, one end (e.g., the distal end) of activation wire 100 may be coupled to the tip of catheter body 202 (e.g., coupled to a distal-most tip electrode of electrodes 210), while the other end (e.g., the proximal end) of activation wire 100 may be coupled to an actuator (e.g., a thumb slider) on handle 212. Thus, for example, sliding the thumb slider proximally can place activation wire 100 in tension, thereby altering the radius of curvature of the loop of distal shaft.

Another exemplary mechanism for varying the radius of curvature of the loop of distal shaft 206 is described in U.S. Pat. No. 7,606,609, which is hereby incorporated by reference as though fully set forth herein.

Figure 3D:
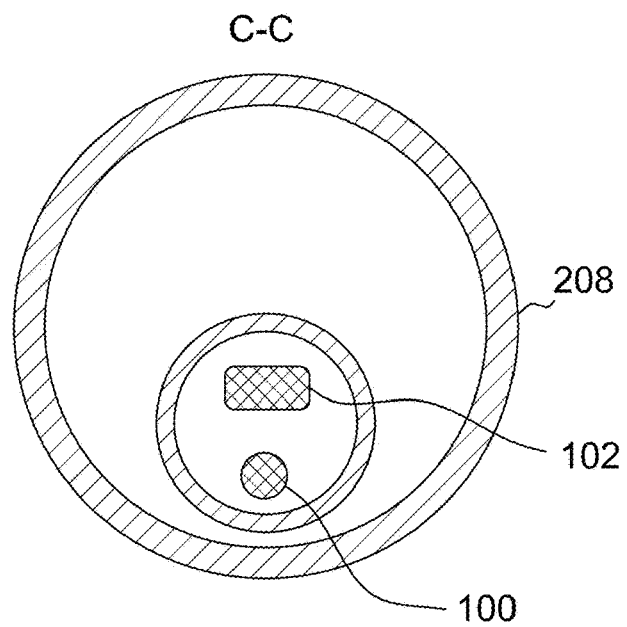
FIG. 3D illustrates a cross section C-C of an example of a distal portion of a catheter.

FIG. 3D also depicts a shaping wire, or pre-formed memory wire 102 as previously described. In one embodiment, this memory wire 102 may extend through neck region 208 and at least partially through distal region 206 in order to help predispose distal region 206 into the loop shape depicted throughout the figures. Memory wire 102 can be made from a shape memory material such as nitinol. When the activation wire 100 is aligned with a second element such as a pre-formed memory wire 102 to cause the distal end of a catheter or other medical device to be in a loop or lasso shape, the activation wire 100 can be tensioned or "pulled" to cause an action to occur to the pre-formed memory wire (e.g., to change the radius of the loop of the pre-formed memory wire). The position of the activation wire 100 and memory wire 102 in FIG. 3D are merely illustrative, and can be positioned in any desired fashion within the catheter.

Figure 4A:
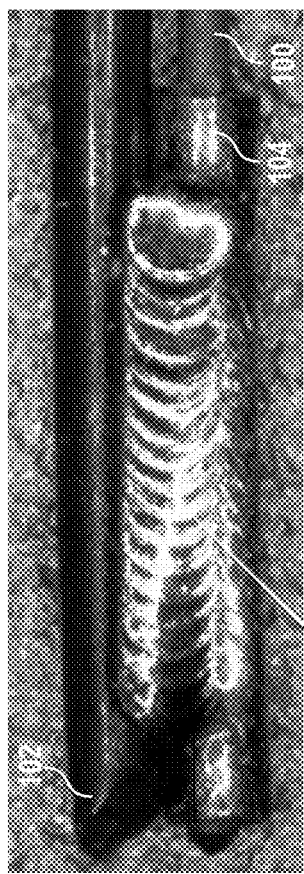
FIGS. 4A-4B illustrate one representative embodiment of attaching an activation wire to a shape-memory wire, utilizing a sleeve, and by laser welding the components.
Figure 4B:
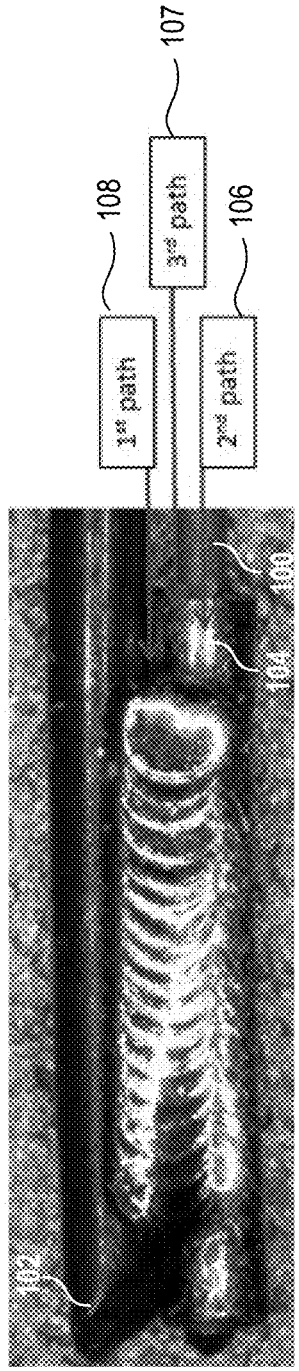

FIGS. 4A-4B illustrate one representative embodiment of attaching an activation wire 100 to a shape-memory wire 102, utilizing a sleeve 104, and by laser welding 106/108 the components as previously described. As shown in FIG. 4A, the activation wire ("pull wire") is covered with a sleeve 104, which is an Inconel™ 600 hypo tube in the illustrated example. The laser welds 106 and 108 described in connection with FIG. 1 are applied, as depicted by laser weld 106/108. The laser weld 106 primarily welds the activation wire 100 to the sleeve 104, and the weld 108 primarily welds a nitinol shape-memory wire 102 to the sleeve 104.

In one representative embodiment, the seam weld length between the nitinol wire 102 and the sleeve 104 is approximately 0.070 inches (0.178 centimeters), while the laser spot size is approximately 0.014 inches (0.036 centimeters). In another representative embodiment, the sleeve 104 and activation wire 100 are held in place using a fixture during the laser welding process.

While the laser welds may be accomplished in any desired manner in accordance with the principles described herein, FIG. 4B depicts one exemplary manner of welding the activation wire 100, nitinol wire 102, and sleeve 104 to attach the activation wire 100 to the nitinol wire 102. This particular example is provided for facilitating an understanding of a manner of attaching these components, but is not limited to any such example. For example, a first path laser beam is aligned with the nitinol wire 102 and the sleeve 104 to create the laser weld 108. In this particular example, a second path laser beam is moved a distance away from the nitinol wire 102, such as 0.008 inches (0.020 centimeters) to center the beam on top of the sleeve 104 as it covers the activation wire 100, to create the laser weld 106. In this particular example, a third path laser beam is moved back towards the nitinol wire 102, such as moved 0.004 inches (0.010 centimeters) back towards the nitinol wire 102, to create a third laser weld 107.

Figure 5A:
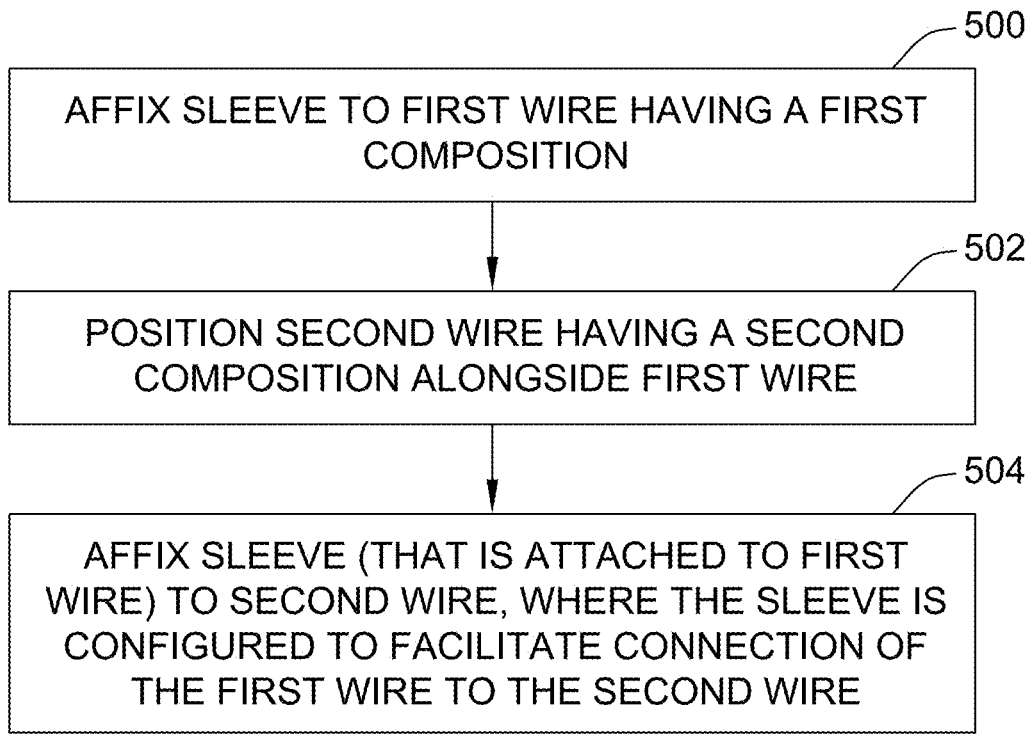
FIGS. 5A and 5B are flowcharts of alternative representative manners of creating an affixed pair of wires having dissimilar compositions.

FIG. 5A is a flowchart of a representative manner of creating an affixed pair of wires having dissimilar compositions, and may also have dissimilar diameters. For example, the wires may include an activation wire and a shape-memory wire for use with a variable loop catheter in accordance with the principles described herein. A sleeve is affixed 500 to a first wire having a first composition. A second wire having a second composition is positioned 502 alongside the first wire. The sleeve that is attached to the first wire is affixed 504 to the second wire, where the sleeve is configured to facilitate connection of the first wire to the second wire.

Figure 5B:
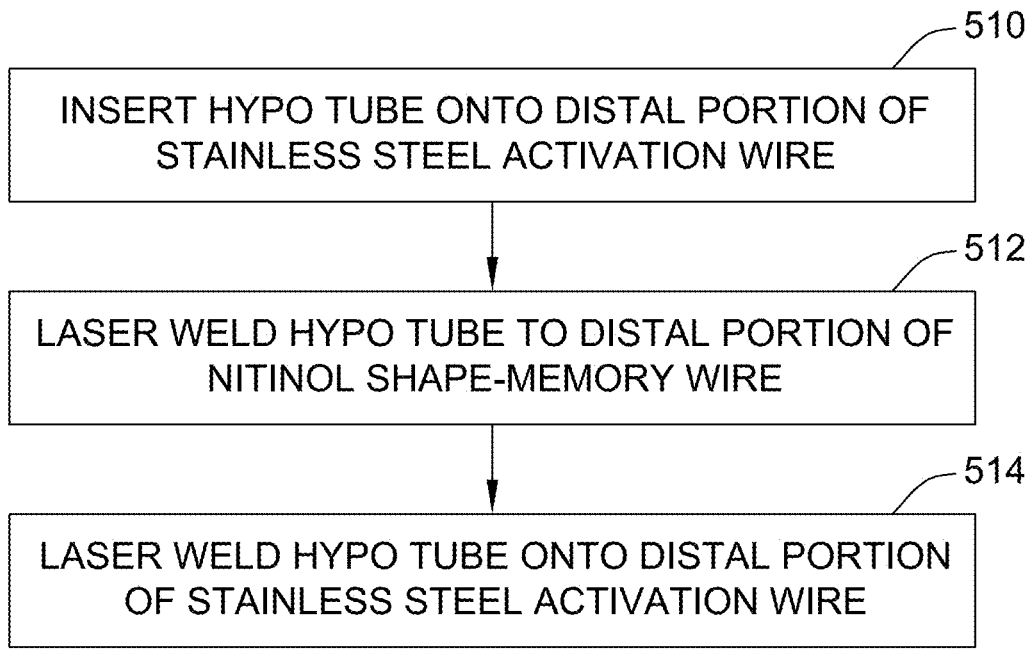

FIG. 5B is a flowchart of another representative manner of affixing wires. In this example, the first wire is represented by a predominantly stainless steel wire, and the second wire is represented by a predominantly nitinol wire. A hypo tube is utilized, where the hypo tube is composed of materials capable of being affixed to both the stainless steel wire and the nitinol wire, such as an Inconel™ 600 hypo tube. The hypo tube is inserted 510 onto the distal portion of the stainless steel activation wire. The hypo tube is laser welded 512 (e.g., laser welding with inert gas assist) to the distal portion of the nitinol shape-memory wire. The hypo tube is laser welded 514 (e.g., laser welded with inert gas assist) onto the distal portion of the stainless steel activation wire. In this manner, the stainless steel activation wire is affixed to the nitinol wire even though they are made from different compositions that otherwise do not readily affix to one another.

Figure 6:
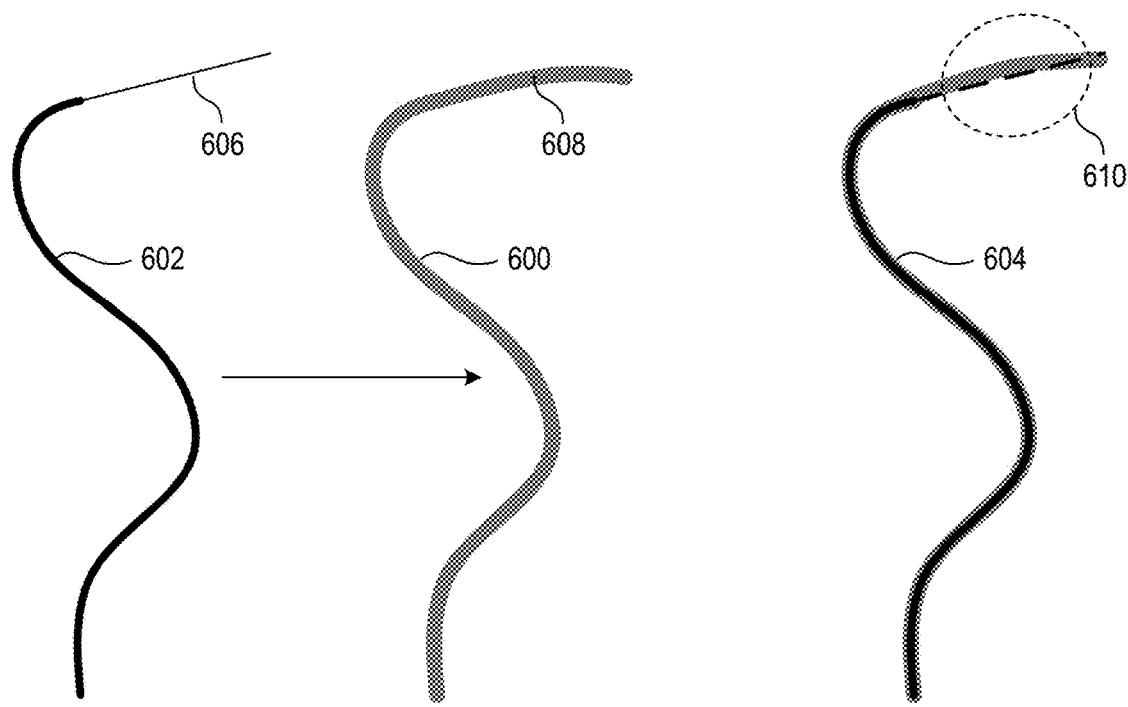
FIG. 6 illustrates an embodiment with a first tether that is to be manipulated by a second structure such as a memory wire.

In another embodiment of the present disclosure, FIG. 6 illustrates an embodiment involving a first structure, such as a first tether or wire 600, that is to be adjusted, controlled, or otherwise manipulated by a second structure, such as a second wire 602. The second wire 602 is formed to be of substantially the same shape as the first wire 600, such that when the two wires 600, 602 are overlaid, they substantially align as depicted by the dual wire structure 604. For purposes of description, the first and second structures may be referred to herein as "wires," although this is intended to include any tethering structure regardless of the material to which it is made. Thus, when referring to "wire," this can be any type of tether including metal, para-aramid synthetic fiber (e.g., Kevlar™), fabric fibers, etc.

In one embodiment, one or more sections 606 of the second wire 602 are adapted to facilitate connection to the first wire 600. For example, the shape of the wire section 606 may be made to deviate from the remaining shape of the wire 602, such as providing a substantially straight or linear wire section 606 that can better connect to a corresponding portion 608 of the first wire 600. In some embodiments, the corresponding portion 608 of the first wire 600 may also be adapted to a corresponding shape of the wire section 606, such as corresponding linear portions that better facilitate coupling the wire section 606 and wire portion 608 to one another. For example, the better alignment of the resulting overlaid portion 610, with corresponding linear shapes, may better facilitate coupling by way of, for example, a crimp, twist-on wire nut, adhesives, solder or other melted metal affixation, etc.

In one embodiment, the wire section 606, whether shaped in a specific manner or not, may be designed to have different external characteristics than a remaining portion of the second wire 602. For example, the wire section 606 may be created to have a higher coefficient of friction than the remaining portion of the second wire 602. This difference in external frictional characteristics can be created in numerous ways. For example, the wire section 606 can be coated with a material(s) that increases its coefficient of friction. In another example, where the second wire 602 is coated with a material to enhance its lubricity (e.g., polytetrafluoroethylene or "PTFE"), this coating may be stripped at the wire section 606. In yet another example, the wire section 606 and remaining portion of second wire 602 may be distinct and separate elements that are affixed to one another, where the wire section 606 has a higher coefficient of friction than the remaining portion of the second wire 602 to which it is attached. Other manners of creating the wire section 606 to have a higher coefficient of friction than the remaining portion of the second 602 may also be implemented.

In one embodiment, the higher coefficient of friction of the wire section 606 is desired to facilitate a better coupling to the corresponding portion 608 of the first wire 600. For example, where the second wire 602 is coated with PTFE, the wire section 606 may be stripped to remove most or all of the PTFE, so that a crimp or other connection of the wire section 606 and wire portion 608 creates the resulting overlaid portion 610 with less chance of failure of the attachment of these two wire sections 606, 608.

Figure 7A:
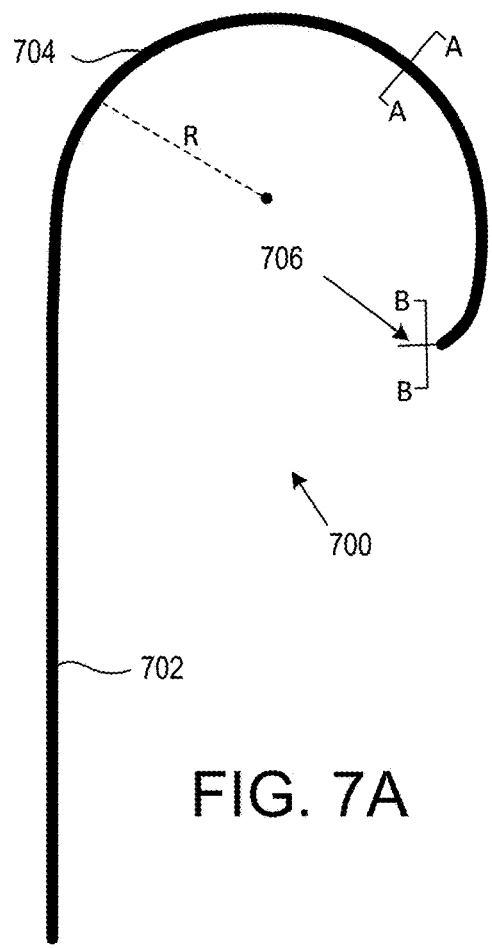
FIG. 7A illustrates another embodiment of an activation wire that is to be formed to structurally correspond to the shape of a second element such as a looped memory wire.

FIG. 7A illustrates a more specific, representative embodiment. In this embodiment, the tether (e.g., wire in this example) that is to be formed to structurally correspond to the shape of a second element (not shown) is an activation wire 700, such as that which may be used in a catheter, introducer, dilator or other intravascular medical device to cause deflection or other movement at a distal portion of the intravascular medical device. The activation wire may also be referred to as a "pull wire" or the like. In the illustrated embodiment, the activation wire 700 includes a first portion 702 that is strung through the body of an elongate body, such as a catheter shaft. The activation wire 700 further includes a formed portion 704, which is formed into a shape that deviates from the shape of the first portion 702, which in this example is a loop or lasso shape. Thus, when this activation wire 700 is aligned with a second element such as a pre-formed memory wire to cause the distal end of a catheter or other medical device to be in a loop or lasso shape, the activation wire 700 can be tensioned or "pulled" to cause an action to occur to the pre-formed memory wire (e.g., to change the radius of the loop of the pre-formed memory wire).

In one embodiment, one or more sections 706 of the activation wire 700 are adapted to facilitate connection to the pre-formed memory wire or other second element (not shown). For example, the shape of the wire section 706 may be formed in substantially straight or linear that can better connect to a corresponding portion of s second element. In some embodiments, the corresponding portion of the second element (not shown) may also be adapted to a corresponding shape of the wire section 706, such as corresponding linear portions that better facilitate coupling these sections. For example, the better alignment may better facilitate coupling by way of, for example, a crimp, twist-on wire nut, adhesives, solder or other melted metal affixation, etc.

In one embodiment, the wire section 706 is designed to have different external characteristics than one or more of the remaining portions 702, 704. For example, the wire section 706 may be created to have a higher coefficient of friction than the remaining portions 702, 704. It may be desirable for portions 702, 704 to have a relatively high lubricity to facilitate movement within, for example, a catheter shaft, while it may be desirable to have a lower lubricity (e.g., higher coefficient of friction) for the wire section 706 to facilitate a better connection to its counterpart pre-formed memory wire or other second element (not shown). As noted above, this difference in external frictional characteristics can be created in numerous ways, including but not limited to coating the wire section 706 with a material(s) that increases its coefficient of friction, and/or stripping or otherwise removing an external lubricious material on the activation wire 700 at the wire section 706 to expose an internal layer having a higher coefficient of friction; and/or coupling a wire section 706 having a desirably high coefficient of friction to the wire portions 702, 704; etc.

Figure 7B:
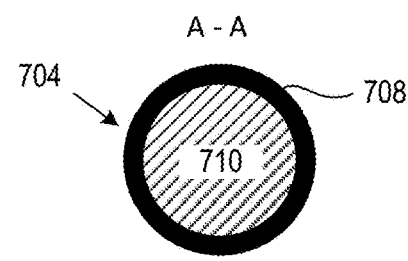
FIG. 7B depicts a distal portion of an activation wire that is coated with a lubricious material.
Figure 7C:
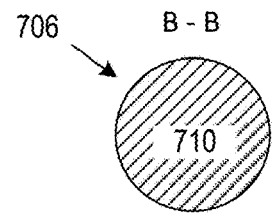
FIG. 7C depicts a distal portion of an activation wire that has had a lubricious coating removed.

In one embodiment, the higher coefficient of friction of the wire section 706 is desired to facilitate a better coupling to a corresponding portion of a second element (e.g., a pre-formed memory wire). For example, where the activation wire 700 is coated with PTFE, the wire section 706 may be stripped to remove most or all of the PTFE, so that a crimp or other connection of the wire section 706 and second element (not shown) creates a coupling with less chance of failure of the attachment. This removal of a lubricious layer is depicted in FIGS. 7B and 7C, which respectively depict cross-sectional views as sections A-A and B-B in FIG. 7A. In FIG. 7B, the wire portion 704 includes a layer 708 having a higher lubricity than an internal layer 710. This higher lubricity layer 708 may be, for example, a PTFE layer. At wire section 706, this higher lubricity layer 708 is stripped or otherwise removed to expose the internal layer 710 that has a lower lubricity (i.e., higher coefficient of friction) to cause the exposed surface to have a higher frictional characteristic. In this manner, the wire section 706 can be better coupled with a corresponding portion of a second element (not shown) to increase the integrity of the coupling.

When coupled to a second element such as a pre-formed memory wire, the activation wire 700 can be tensioned or pulled manually, robotically, etc. When tensioned in this manner, the attached portion (the wire section 706 at the distal end of the activation wire and second element in this example) tensions the coupled pre-formed memory wire, causing the radius R of the activation wire and corresponding second element to be reduced.

Figure 8A:
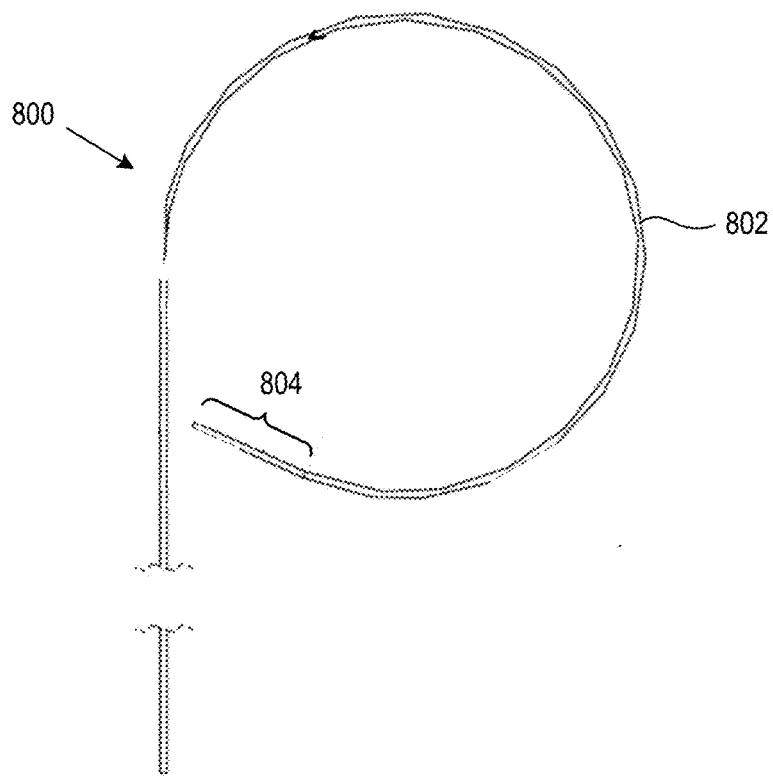
FIGS. 8A and 8B depict embodiments of activation wires formed in a loop or lasso structure at their distal ends, and having a linear portion to facilitate connection to a pre-formed memory wire used at the distal end of an intravascular medical device.
Figure 8B:
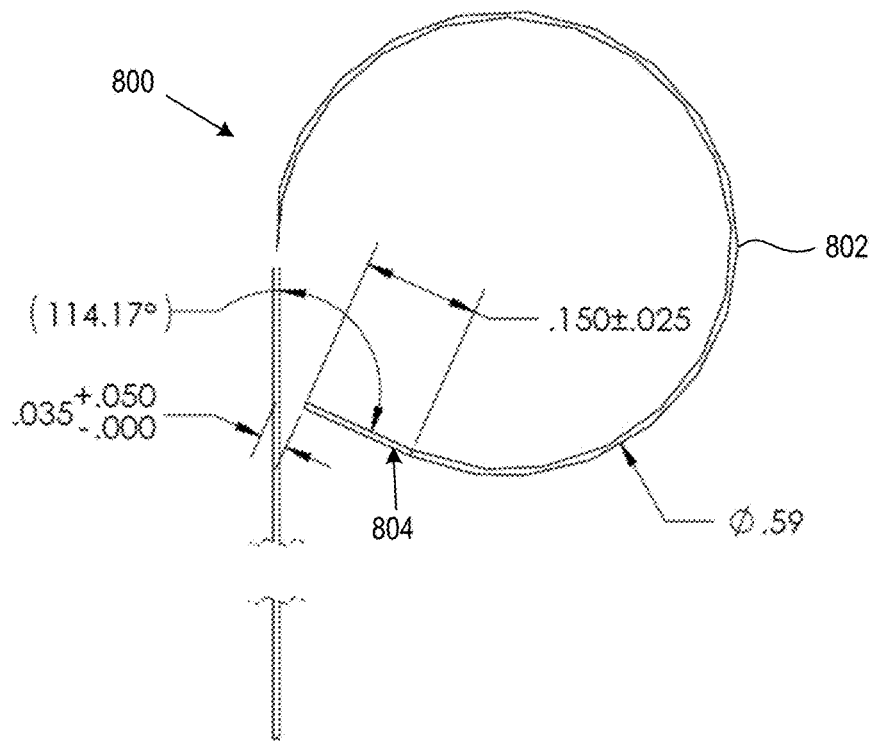

FIG. 8A illustrates an activation wire 800 as previously described, formed in a loop or lasso structure 802 at its distal end, and having a linear portion 804 to facilitate connection to a second structure such as a pre-formed memory wire (not shown) that may be used at the distal end of a catheter or other intravascular medical device. The linear portion 804 may be made to have a higher coefficient of friction than the remaining portion of the activation wire 800. FIG. 8B illustrates one representative example of dimensions of such an activation wire.

Referring now to the figures, FIGS. 9A and 9B depict two representative embodiments of an electrophysiology (EP) catheter 900 into which the tether coupling embodiments described herein and associated principles may be implemented. EP catheter 900 includes an elongate catheter body 902, which, in some embodiments, is tubular (e.g., it defines at least one lumen therethrough). Catheter body 902 includes a proximal region 904, a distal region 906, and a neck region 908 that offers a transition from proximal region 904 to distal region 906. In some embodiments, neck region 908 can include a coupling, such as described in U.S. provisional application No. 62/280,159, filed Jan. 19, 2016, which is hereby incorporated by reference as though fully set forth herein. The relative lengths of proximal region 904, distal region 906, and neck region 908 as depicted in FIGS. 6 and 7 are merely illustrative and may vary without departing from the spirit and scope of the instant disclosure. The overall length of catheter body 902 should be long enough to reach the intended destination within the patient's body.

Catheter body 902 may be made of a biocompatible polymeric material, such as PTFE tubing (e.g., TEFLON® brand tubing). Of course, other polymeric materials, such as fluorinated ethylene-propylene copolymer (FEP), perfluoro-alkoxyethylene (PFA), poly(vinylidene fluoride), poly(ethylene-co-tetrafluoroethylene), and other fluoropolymers, may be utilized. Additional suitable materials for catheter body 902 include, without limitation, polyamide-based thermoplastic elastomers (namely poly(ether-block-amide), such as PEBAX®), polyester-based thermoplastic elastomers (e.g., HYTREL®), thermoplastic polyurethanes (e.g., PELLETHANE®, ESTANE®), ionic thermoplastic elastomers, functionalized thermoplastic olefins, and any combinations thereof. In general, suitable materials for catheter body 402 may also be selected from various thermoplastics, including, without limitation, polyamides, polyurethanes, polyesters, functionalized polyolefins, polycarbonate, polysulfones, polyimides, polyketones, liquid crystal polymers and any combination thereof. It is also contemplated that the durometer of catheter body 902 may vary along its length. The basic construction of catheter body 902 will be familiar to those of ordinary skill in the art, and thus will not be discussed in further detail herein except to the extent necessary to understand the instant disclosure.

Figure 9C:
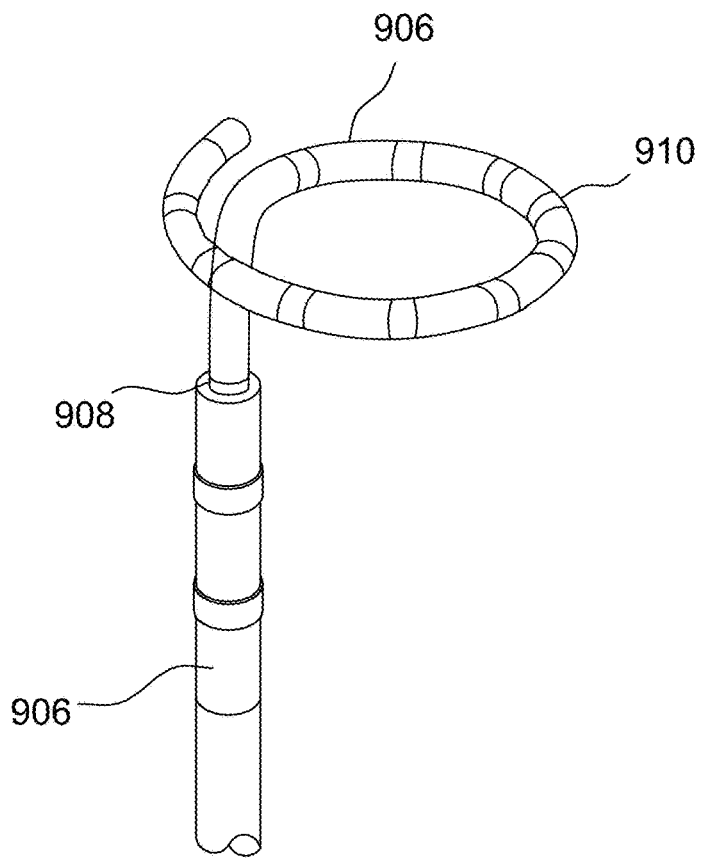
FIG. 9C illustrates a representative distal region of a catheter having multiple electrodes and being predisposed into at least a partial loop.

As seen in FIG. 9C, distal region 906 of catheter body 902 can be predisposed into at least a partial loop. This loop shape allows distal region 906 to conform to the shape, for example, of a pulmonary vein ostium. The partial loop may take a number of configurations, depending on the intended or desired use of EP catheter 900, consistent with the present teachings. Therefore, it should be understood that the loop configuration depicted in FIG. 9C is merely illustrative.

FIG. 9C also illustrates that distal region 906 can include a plurality of electrodes 910 disposed thereon. Electrodes 910 may be ring electrodes or any other electrodes suitable for a particular application of EP catheter 900. For example, where EP catheter 900 is intended for use in a contactless electrophysiology study, electrodes 900 may be configured as described in U.S. application Ser. No. 12/496,855, filed 2 Jul. 2009, which is hereby incorporated by reference as though fully set forth herein. Of course, in addition to serving sensing purposes (e.g., cardiac mapping and/or diagnosis), electrodes 900 may be employed for therapeutic purposes (e.g., cardiac ablation and/or pacing).

Referring again to FIGS. 9A and 9B, FIGs, a handle 912 is coupled to catheter body 902, for example at the proximal end of proximal region 904. Handle 912 can include suitable actuators (e.g., actuator 914A in FIG. 9A; actuator 914B in FIG. 9B) to control the deflection of catheter body 902, for example as described in U.S. Pat. No. 8,369,923, which is hereby incorporated by reference as though fully set forth herein. Actuators 914A or 914B, or other actuators (not shown) may be utilized to alter the radius of the distal region 906. For example, an actuator different from actuators 914A, 914B may be included on the handle where manipulation of this actuator causes a loop in the distal region 906 of the catheter 900 to increase or decrease. Various handles and their associated actuators for use in connection with electrophysiology catheters are known, and thus handle 912 will not be described in further detail herein. Further, other mechanisms may be utilized to actuate the loop structure, such as robotic mechanisms.

In embodiments described herein, the radius of curvature of the loop of distal region 906 may be adjustable, for example to conform to the varying sizes of pulmonary vein ostia of patients of different ages. This additional control may be provided, for example, via the use of an activation wire 916, shown in FIG. 9D that is adapted to alter the radius of curvature of the loop of distal region 906. Activation wire 916 corresponds to activation wires 602, 700 and 800 in FIGS. 6, 7A, 7B, 7C, 8A and 8B. One suitable material for activation wire 916 is stainless steel, though other materials can be employed without departing from the spirit and scope of the instant disclosure.

In some embodiments, one end (e.g., the distal end) of activation wire 916 may be coupled to the tip of catheter body 902 (e.g., coupled to a distal-most tip electrode of electrodes 910), while the other end (e.g., the proximal end) of activation wire 916 may be coupled to an actuator (e.g., a thumb slider) on handle 912. Thus, for example, sliding the thumb slider proximally can place activation wire 916 in tension, thereby altering the radius of curvature of the loop of distal region 906.

Another exemplary mechanism for varying the radius of curvature of the loop of distal region 906 is described in U.S. Pat. No. 7,606,609, which is hereby incorporated by reference as though fully set forth herein.

Figure 9D:
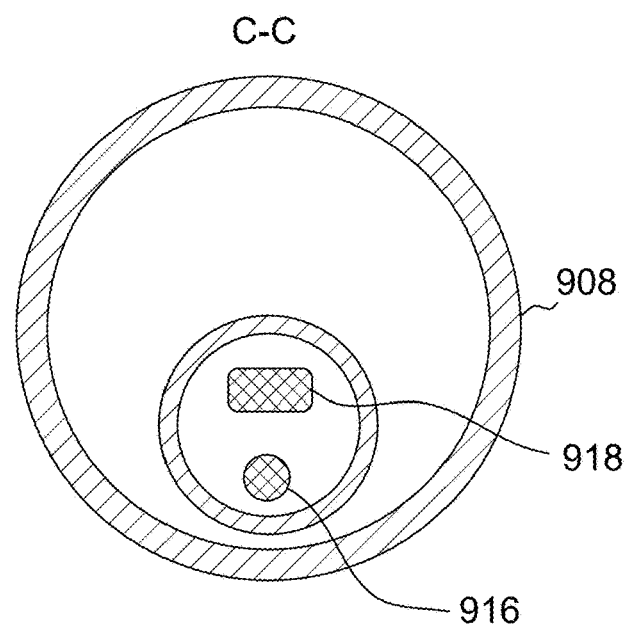
FIG. 9D illustrates a cross section C-C of an example of a distal portion of a catheter.

FIG. 9D also depicts a shaping wire, or pre-formed memory wire as previously described. In one embodiment, this memory wire 918 extends through neck region 908 and at least partially through distal region 906 in order to help predispose distal region 906 into the loop shape depicted throughout the figures. Memory wire 918 can be made from a shape memory material such as nitinol.

Figure 10A:
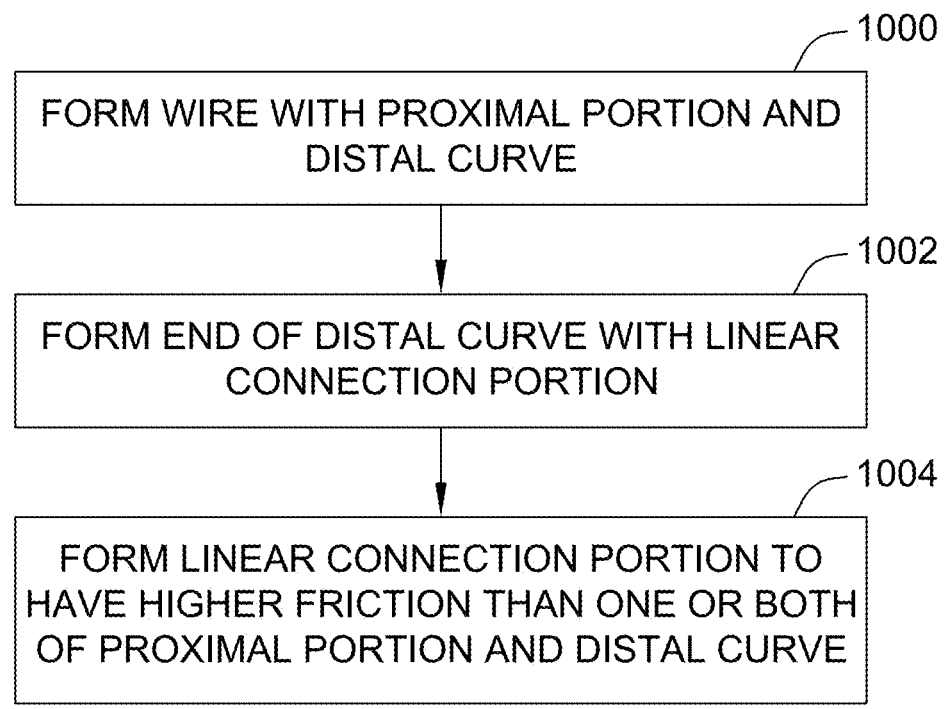
FIG. 10A is a flowchart of a representative manner of creating an activation wire for use with a variable loop catheter in accordance with the principles described herein.

FIG. 10A is a flowchart of a representative manner of creating an activation wire for use with a variable loop catheter in accordance with the principles described herein. An activation wire (including any type of tether) is formed 1000 with a proximal portion and a distal curve. The end of the wire is formed 1002 with a linear connection portion. At least a portion of the linear connection portion is formed 1004 to have a higher friction than one or both of the proximal portion and distal curve.

Figure 10B:
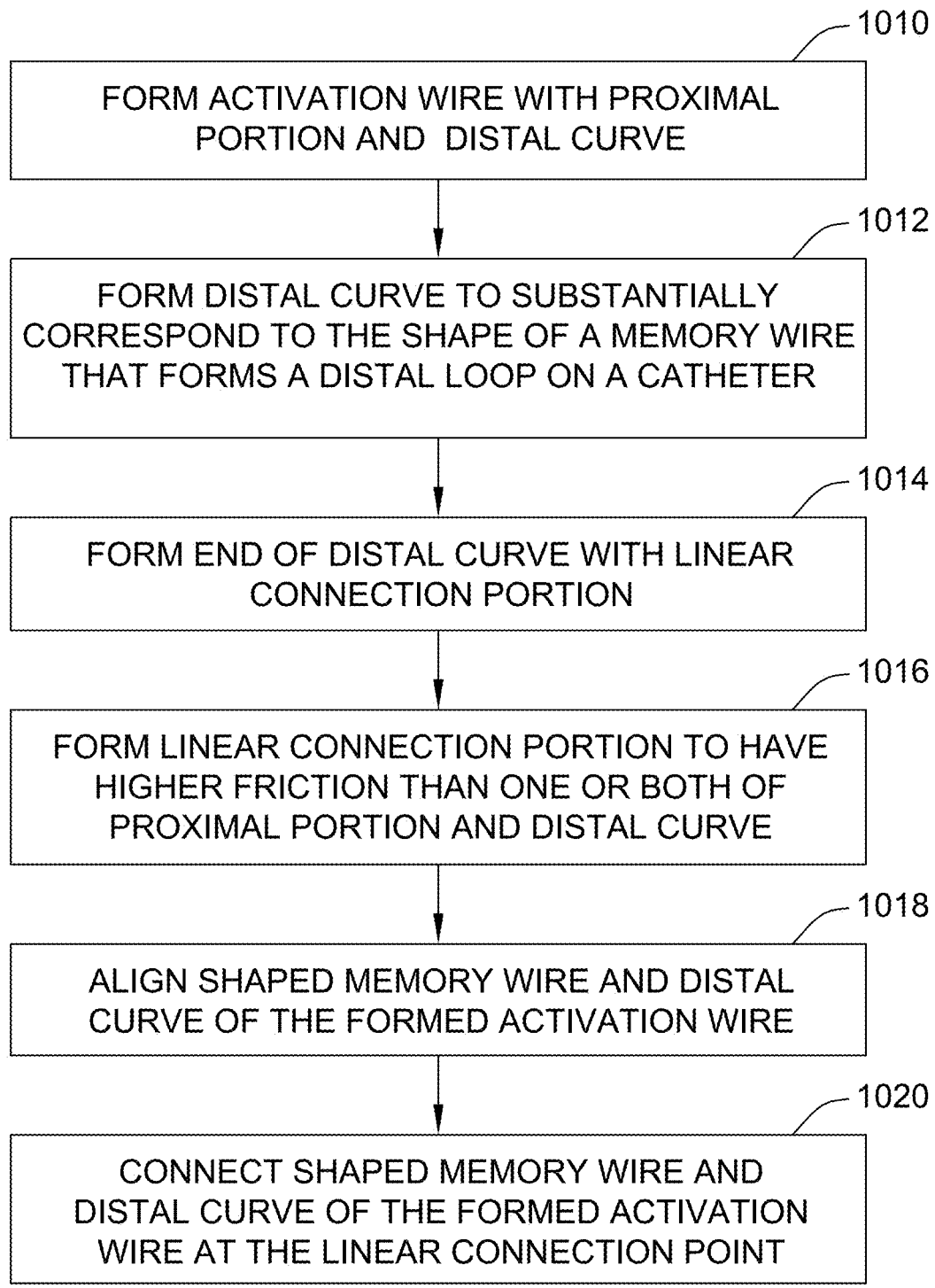
FIG. 10B is a flowchart of a representative manner of creating an activation wire for use with a variable loop catheter, and utilizing it in connection with a looped memory wire to form an adjustable distal loop portion in a catheter.

FIG. 10B is a flowchart of a representative manner of creating an activation wire for use with a variable loop catheter, and utilizing it in connection with a looped memory wire to form an adjustable distal loop portion in a catheter. An activation wire (including any type of tether) is formed 1010 with a proximal portion and a distal curve (optionally, in some embodiments, the distal curve may be a distal linear portion without any curve). The distal curve is formed 1012 to substantially correspond to the shape of a memory wire that forms a distal loop on a catheter. The end of the distal curve is formed 1014 with a linear connection portion. The linear connection portion is formed 1016 to have a higher coefficient of friction than the proximal portion and/or the distal curve. The shaped memory wire and distal curve of the activation wire are aligned 1018, and the shaped memory wire and distal curve of the formed activation wire are connected 1020 at the linear connection point. It should be recognized that the connection portion need not be linear as in this example, but may be any shape that facilitates connection between the shaped memory wire and the distal curve of the activation wire.

Although several embodiments have been described above with a certain degree of particularity, those skilled in the art could make numerous alterations to the disclosed embodiments without departing from the spirit or scope of the disclosure.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter, comprising:
    a shaft having a proximal portion and a distal portion;
    a pre-formed loop wire having a variable radius and positioned within the distal portion of the shaft to form a loop structure on the distal portion of the shaft;
    a stainless steel pull wire comprising a proximal section and a distal section, wherein the distal section of the stainless steel pull wire is at least partially positioned in the loop structure on the distal portion of the shaft; and
    a nickel superalloy sleeve comprising an internal surface and an external surface, the distal section of the stainless steel pull wire bonded to the internal surface of the nickel superalloy sleeve with a first laser weld, and the pre-formed loop wire bonded to the external surface of the nickel superalloy sleeve with a second laser weld.

2. The catheter of claim 1, wherein the pre-formed loop wire is comprised of nickel titanium.

3. The catheter of claim 2, wherein the pre-formed loop wire has a different diameter than the stainless steel pull wire.

4. A catheter, comprising: a shaft having a proximal portion and a distal portion;
    a pre-formed loop wire having a variable radius and positioned within the distal portion to form a loop structure on the distal portion of the shaft;
    an activation wire comprising a proximal section and a distal section, wherein the distal section of the activation wire is at least partially positioned in the loop structure on the distal portion of the shaft, wherein the activation wire further comprises a linear connection section on the distal section having an external surface with a higher coefficient of friction than at least one of the proximal section and a remaining portion of the distal section that does not include the connection section; and
    a connecting element comprising an internal surface and an external surface, the linear connection section of the activation wire coupled to the internal surface, an aligned portion of the pre-formed loop wire coupled to the external surface, wherein the connecting element coupled to the linear connection section and the aligned portion of the pre-formed loop wire enables adjustment of the variable radius in response to manipulation of the activation wire.

5. The catheter of claim 1, wherein the pre-formed loop wire is a wire predisposed in a loop shape in an unbiased state.

6. The catheter of claim 4, wherein the pre-formed loop wire is a wire predisposed in a loop shape in an unbiased state.

* * * * *